US005578576A

United States Patent [19]
Leddin

[11] Patent Number: 5,578,576
[45] Date of Patent: Nov. 26, 1996

[54] METHOD AND COMPOSITION FOR TREATING INTESTINAL WOUNDS OR ULCERS

[75] Inventor: Desmond Leddin, Nova Scotia, Canada

[73] Assignee: Dalhousie University, Nova Scotia, Canada

[21] Appl. No.: 300,428

[22] Filed: Sep. 2, 1994

[51] Int. Cl.$^6$ .......................... A61K 38/16; A61K 38/01; A61K 38/04; A61K 31/70

[52] U.S. Cl. .................... 514/21; 514/2; 514/12; 514/23; 514/925; 514/926; 514/927; 424/439

[58] Field of Search ................... 514/2, 12, 21, 514/23, 925, 926, 927; 424/439

[56] References Cited

U.S. PATENT DOCUMENTS

| | | | |
|---|---|---|---|
| 4,414,238 | 11/1983 | Schmidl | 426/602 |
| 4,847,296 | 7/1989 | Babayan et al. | 514/552 |
| 5,214,066 | 5/1993 | Szabo | 514/423 |
| 5,221,668 | 6/1993 | Henningfield et al. | 514/23 |
| 5,223,284 | 6/1993 | Kulczycki, Jr. et al. | 426/42 |
| 5,240,909 | 8/1993 | Nitsche | 424/85.1 |

FOREIGN PATENT DOCUMENTS

| | | |
|---|---|---|
| 1226817 | 9/1987 | Canada. |
| 1227429 | 9/1987 | Canada. |
| 1318592 | 6/1993 | Canada. |
| 0292699 | 11/1988 | European Pat. Off.. |
| WO92/17189 | 10/1992 | WIPO. |
| WO93/19747 | 10/1993 | WIPO. |

OTHER PUBLICATIONS

Law et al. "The Effect of Dietary Protein Depletion on Immunocompetence" Ann Surg. 179(2) 168–173 1974.
Gitnick "Current Gastroenterology" pp. 32–49 1985.
Mulder, Food and animal feed additives containing manganese—to promote growth of intestinal lactic acid bacteria, e.g. for prophylaxis of diabetes, WPAT Abstracts, Abstract No. 93–203368/25.

Serhan et al, Use of lipoxin and its derivatives as antagonists for SRS–A especially LTD—for control of haemostasis, vasoconstriction, anaphylactic and allergic reactions in animals, WPAT Abstracts, Abstract No. 90–361242/48.
Brooks et al, New substd. furan and pyrrole cpds.—are inhibitors of 5– and/or 12–lipoxygenase activity which orally prevent in vivo biosynthesis of leukotriene(s), WPAT Abstracts, Abstract No. 89–165598/22.
Diamantstein et al, Monoclonal antibodies recognizing human interleukin–2 receptors—useful in therapy of hyperimmune syndrome diseases, for coupling to cytotoxic agents and in diagnosis of the receptors in or on cells, WPAT Abstracts, Abstract No. 87–286562/41.
Johnson et al, Extract of Tanacetium parthenium—containing sesqui:terpene lactone(s) for treating migraine and arthritic and bronchial disorders, WPAT Abstracts, Abstract No. 84–011818/03.
Ueda et al, Drug for Protecting Gastrointestinal Cell, JAPIO Abstracts, Abstract No. 85–013714.
Zimmermann et al, Insulin–like growth factor I and interleukin 1.beta messenger RNA in a rat model of granulomatous enterocolitis and hepatitis, Chemical Abstracts, Abstract No. CA119–223219(21).

(List continued on next page.)

Primary Examiner—Mindy Fleisher
Assistant Examiner—Nancy J. Degen
Attorney, Agent, or Firm—Hill, Steadman & Simpson

[57] ABSTRACT

The present invention provides a method for aiding healing or preventing the onset of intestinal wounds or ulcers in a patient. In addition, the present invention provides a method for reducing, or preventing, the gastrointestinal side effects associated with the administration of a nonsteroidal antiinflammatory drug. Pursuant to the present invention, the composition includes a protein source, a carbohydrate source, a fat source, and a specialized vitamin and mineral profile.

19 Claims, 12 Drawing Sheets

OTHER PUBLICATIONS

Auler et al, *Antibodies of IgG2 subtype are involved in the immunological inflammatory response of TNBS–induced enteritis in rats,* Chemical Abstracts, Abstract No. CA119–070240(07).

Mitchell et al, *Effect of the immune modulating agents cyclophosphamide, methotrexate, hydrocortisone, and cyclosporin A on an animal model of granulomatous bowel disease,* Chemical Abstracts, Abstract No. CA113–091119(11).

Wallace et al, *An orally active inhibitor of leukotriene synthesis accelerates healing in a rat model of colitis,* Chemical Abstracts, Abstract No. CA113–034472(05).

Allison et al, *Gastrointestinal Damage Associated With the Use of Nonsteroidal Antiinflammatory Drugs,* The New England Journal of Medicine, vol. 327, No. 11, pp. 749–754 (1992).

Bjarnason et al, *Clinicopathological Features of Nonsteroidal Antiinflammatory Drug–Induced Small Intestinal Strictures,* Gastroenterology, vol. 94, No. 4, pp. 1070–1074 (1988).

Bjarnason et al, *Nonsteroidal Antiinflammatory Drug–Induced Intestinal Inflammation in Humans,* Gastroenterology, vol. 93, No. 3, pp. 480–489 (1987).

Fang et al, *Indomethacin–Induced Intestinal Inflammation,* Digestive Diseases, vol. 22, No. 9, pp. 749–760 (1977).

Matsumoto et al, *Effects of diet on experimentally induced intestinal ulcers in rats: morphology and tissue leukotrienes,* Gut, vol. 35, pp. 1058–1063 (1994).

Alder et al, *Enteral Formula Composition Does Not Affect Response to Lethal Infectious Challenge in Mice,* J. Nutr., vol. 124, pp. 2156–2162 (1994).

METHOD AND COMPOSITION FOR TREATING INTESTINAL WOUNDS OR ULCERS

BACKGROUND OF THE INVENTION

The present invention relates generally to the treatment and nutritional support of patients. More specifically, the present invention relates to the treatment of patients suffering from intestinal wounds or ulcers or at risk of same.

An ulcer is a common inflammatory lesion in which a loss or destruction of superficial tissue exists. Ulcers occur in several locations as acute, sub-acute, chronic or recurrent types. In each location, some initiating factor, such as action of bacterial toxins or lack of oxygen, causes death of the surface tissue. This necrotic tissue then usually sloughs off, leaving the underlying area exposed to further damage.

Peptic ulcers are a common form of ulcers that occur in the upper gastrointestinal tract. Peptic ulcer is defined as a circumscribed ulceration of the mucous membrane penetrating through the muscularis mucosa and occurring in areas exposed to acid and pepsin. The loss of the mucosa, ordinarily covered by a mucous secretion, lays bare the musculo-membranous wall. Peptic ulcers occur most commonly in the first few centimeters of the duodenum (duodenal ulcers) and along the lesser curvature of the stomach (gastric ulcers). See *The Merck Manual*, 16th Edition, p. 768.

While the peptic ulcer continues to be a common ailment in the general population, the immediate cause of such ulcer remains unknown. Emotional tension and certain physiological patterns are frequently present in affected individuals. Many influences may disturb the balance between ulcer-promoting factors (e.g., secretion of acid or pepsin into the stomach) and factors protecting the mucosal lining of the esophagus, stomach or duodenum (e.g., mucous production, membrane barriers to permeability, and replacement of shed or damaged mucosal cells). See *The Merck Manual*, 16th Edition, p. 768.

Ulcerative colitis of the large intestine is similar, in many respects, to peptic ulcer, because its exact cause is also unknown. Ulcerative colitis is defined as a chronic, non-specific, inflammatory and ulcerative disease arising in the colonic mucosa and is characterized most often by bloody diarrhea. The disease usually begins in the rectosigmoid area and may extend proximally, eventually to involve the entire colon, or it may include most of the large bowel at once. See *The Merck Manual*, 16th Edition, p. 834.

Similar to ulcerative colitis, intestinal ulceration and stricture formation are also characteristic of the inflammatory bowel disease, Crohn's disease. Crohn's disease is defined as a non-specific chronic transmural inflammatory disease that most commonly effects the distal ileum and colon. See *Merck Manual*, 16th Edition, p. 830. However, it may also occur in other parts of the GI tract. The disease is common and causes inflammation of the small intestine and large bowel.

While the immediate causes for intestinal ulcers and wounds remain uncertain, such ulcers and wounds are known to be the adverse side effect of certain drug treatments. For instance, many nonsteroidal anti-inflammatory drugs (NSAIDs) are known to cause gastrointestinal side effects. Single or multiple ulcerations, including perforation and hemorrhage of the esophagus, stomach, duodenum or small and large intestine, have been reported in patients receiving such NSAIDs. See *Physicians' Desk Reference*, 48th Edition, p. 1473.

Prevalent areas subject to ulceration seem to be the stomach and small intestine. Patients who take NSAIDs have an increased risk of mucosal damage in the upper gastrointestinal tract. Many nonsteroidal anti-inflammatory drugs (NSAIDs) cause small intestinal inflammation that may lead to ulceration, perforation and death. See Bjarnason et al, *Nonsteroidal Antiinflammatory Drug-Induced Intestinal Inflammation in Humans*, Gastroenterology, Vol. 93, No. 3, pp. 480–489 (1987). Recent studies have shown that 70% of patients on long-term NSAIDs develop small intestinal inflammation. See Bjarnason et al, *Clinicopathological Features of Nonsteroidal Antiinflammatory Drug-Induced Intestinal strictures*, Gastroenterology, Vol. 94, No. 4, pp. 1070–1074 (1988). Studies have shown a link between the use of NSAIDs and serious complications of peptic ulcer disease. Allison et al, *Gastrointestinal Damage Associated with the Use of Nonsteroidal Antiinflammatory Drugs*, The New England Journal of Medicine, Vol. 327, No. 11, pp. 749–753 (1992).

The pathogenesis of the intestinal inflammation is incompletely understood but thought to involve several interacting factors. Increased intestinal permeability is evident within hours of NSAID ingestion. Researchers have suggested that this exposes the mucosa to luminal macromolecules and toxins. In conjunction with the effect of NSAIDs on chemotaxis and neutrophil function, this may make way for bacterial invasion and hence inflammation. Id.

In addition to small intestinal ulceration, gastrointestinal bleeding without obvious ulcer formation and perforation of pre-existing sigmoid lesions (diverticulum, carcinoma, etc.) have occurred in patients receiving NSAIDs. Researchers have also reported increased abdominal pain in ulcerative colitis patients as well as the development of ulcerative colitis and regional ileitis to occur rarely. See *Physicians' Desk Reference*, 48 Edition, p. 1473.

Still further, researchers have reported that ingested NSAIDs may cause a nonspecific colitis (in particular, fenemates), and many patients with collagenous are taking NSAIDs. NSAIDs may also cause relapse of classic inflammatory bowel disease and contribute to serious complications of diveticular disease (fistula and perforation). Bjarnason et al, *Side Effects on Nonsteroidal Anti-inflammatory Drugs on the Small and Large Intestine in Humans*, Gastroenterology, 104 (6), pp. 1832–47 (1993).

Although it is well known that NSAIDs cause or aggravate intestinal ulcers or wounds in humans, few researchers have addressed ways to prevent or reduce this adverse side effect in patients receiving such drugs. Nevertheless, NSAIDs continues to be the primary recommended drug treatment for various arthritis patients, such as patients suffering from rheumatoid arthritis, ankylosing spondylitis and osteoarthritis. As a result thereof, patients receiving such NSAIDs as a treatment for their arthritic condition often must endure the adverse gastrointestinal side effects of such drugs.

Therefore, a need exists for a method of aiding healing or preventing the onset of intestinal wounds or ulcers in a patient at risk of same.

SUMMARY OF THE INVENTION

The present invention provides a method for treating intestinal wounds or ulcers in a patient. Additionally, the present invention provides a method for reducing or preventing gastrointestinal side effects associated with the treatment of nonsteroidal anti-inflammatory drugs.

In an embodiment, the present invention provides a method for aiding healing or preventing the onset of intestinal wounds or ulcers in a patient. The method includes the step of administering to the patient a therapeutically effective amount of an enteral composition.

Pursuant to the present invention, the enteral composition includes: a protein source comprising approximately 14% to about 25% of the total calories; a carbohydrate source comprising approximately 40% to about 60% of the total calories; and a fat source comprising approximately 30% to about 44% of the total calories. The fat source includes a source of medium chain triglycerides such that the composition has a medium chain triglyceride to long chain triglyceride (MCT:LCT) ratio of approximately 1:4 to 4:1. Preferably, the composition also includes a source of vitamins and minerals including approximately 75% to about 150% of the United States recommended daily allowance per 1500 Kcal of composition administered.

A suitable protein source pursuant to the present invention can be intact or hydrolyzed protein. In addition, the protein source may be either whey or casein.

In an embodiment, the carbohydrate source is either maltodextrin or corn starch.

In an embodiment, the composition includes fractionated coconut oil as a suitable medium chain triglyceride source.

In an embodiment, approximately 25% to about 75% of the fat source consists of medium chain triglycerides.

In an embodiment, the patient is at risk of intestinal wounds or ulcers due to the nonsteroidal anti-inflammatory drug the patient is receiving. In an embodiment, the nonsteroidal anti-inflammatory drug is indomethacin.

The present invention also provides a method of inhibiting the gastrointestinal side effects suffered by a patient receiving a nonsteroidal anti-inflammatory drug. The method includes the step of administering to a patient receiving the nonsteroidal anti-inflammatory drug a therapeutically effective amount of a composition comprising: a protein source; a carbohydrate source; a fat source; and a source of vitamins and minerals. The protein source comprises approximately 14% to about 25% of the total calories. The carbohydrate source comprises approximately 40% to about 60% of the total calories. And, the fat source comprises approximately 33% to about 44% of the total calories. The fat source has a MCT:LCT ratio of approximately 1:4 to 4:1. The composition further includes a source of vitamins and minerals including approximately 75% to about 150% of the recommended daily allowance per 1500 Kcal of the composition administered.

Still further, the present invention provides a method for treating a patient suffering from arthritis, such as rheumatoid arthritis, ankylosing spondylitis or osteoarthritis. The method comprises the step of administering to the patient a nonsteroidal anti-inflammatory drug in combination with the enteral composition of the present invention to reduce the gastrointestinal side effects of the nonsteroidal anti-inflammatory drug.

An advantage of the present invention is that it prevents the onset of intestinal wounds or ulcers in a patient at risk of same.

Moreover, an advantage of the present invention is that it aids in the healing of intestinal wounds or ulcers in a patients suffering from same.

Another advantage of the present invention is that it provides a new method for inhibiting the gastrointestinal side effects associated with the use of nonsteroidal anti-inflammatory drugs. As a result, nonsteroidal anti-inflammatory drugs, such as indomethacin, can be more effectively use in the treatment of arthritis.

Furthermore, an advantage of the present invention is that it provides a new method for treating arthritis that prevents the adverse gastrointestinal side effects commonly associated with such treatments.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

Figure 1:
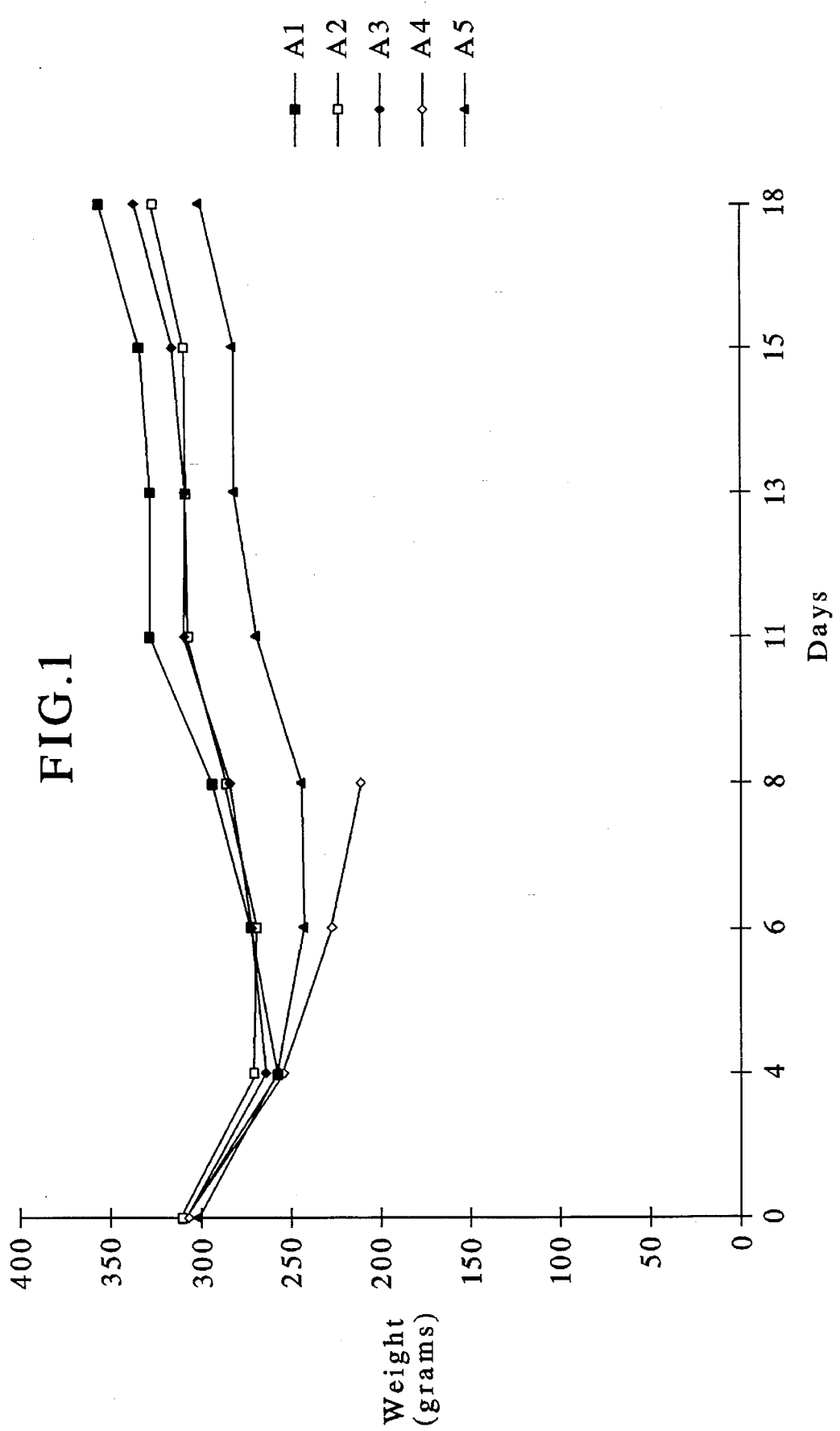
FIGS. 1–3 illustrate the individual weights in weight (grams) versus days of tested rats treated with Peptamen®, Nutren® and standard rat chow, respectively, pursuant to Experiment No. 2.

Intestinal wounds or ulcers can occur due to a number of possible causes and insults. For example, intestinal lesions and ulcers may develop in patients receiving nonsteroidal anti-inflammatory drugs.

Such nonsteroidal anti-inflammatory drugs are of proven value in various forms of arthritis. Among others, the following NSAIDs have been recommended for patients suffering from arthritis: salicylates; indomethacin; ibuprofen; naproxen; fenoprofen; tolmetin; sulindac; meclofenamate; ketoprofen; piroxicam; and diclofenac. Unfortunately, however, tolerance or potential toxic risks rather than marginal differences in efficacy dictate the drug choice. Patients receiving such NSAIDs have an increased risk of mucosal damage in the upper gastrointestinal tract.

Indomethacin is a common nonsteroidal drug with anti-inflammatory, antipyretic and analgesic properties. An untoward effect of indomethacin therapy is gastrointestinal bleeding and ulceration. Such bleeding and ulceration increases with larger doses of indomethacin. As a result, this dose dependency thereby limits the therapeutic approaches that can be taken with such a compound.

The inventor believes that the use of an enteral diet when administered to a patient at risk of intestinal wounds or ulcers will reduce or prevent such conditions. Specifically, the inventor believes that the use of a composition containing protein, carbohydrate and fat sources as well as a source of vitamins and minerals will be effective in the treatment of intestinal ulceration.

The protein source includes approximately 14% to about 25% of the total calories of the composition. In a preferred embodiment, proteins provide approximately 16% of the caloric content of the composition. The protein source may include either hydrolyzed or intact protein. In addition, the protein source may be either whey or casein. In an embodiment, hydrolyzed proteins, such as hydrolyzed lactobumin extracted from whey, can be utilized pursuant to the present invention.

Carbohydrates provide approximately 40% to about 60% of the caloric content of the composition. In a preferred embodiment, carbohydrates provide approximately 51% of the caloric content. A number of carbohydrates can be used including maltodextrin or hydrolyzed corn starch.

The fat content is approximately 33% to about 44% of the caloric content of the composition. In a preferred embodiment, the fat content comprises approximately 33% of the total caloric content of the composition.

Preferably, the fat source has a MCT:LCT ratio of 1:4 to 4:1. In an embodiment, approximately 25 to 75% of the fat source consists of medium-chain triglycerides. In a preferred embodiment, the medium chain triglyceride source is fractionated coconut oil.

In an embodiment, the fat source of the composition includes a source of omega-3 and a source of omega-6 fatty acids. Preferably, the omega-6 to omega-3 fatty acid ratio is approximately 4:1.

In addition, the present invention preferably includes a specialized vitamin and mineral profile. The composition includes a source of vitamins and minerals including approximately 75% to about 150% of the recommended daily allowance per 1500 Kcal of the composition administered. In an embodiment, ultra-trace minerals, such as carnitine and taurine, are included in the composition.

The composition of the present invention is a ready-to-use enteral formulation. The composition can be tube-fed to a patient, or fed by having the patient drink same. Preferably, the caloric density of the composition is 1.0 Kcal per Ml.

The composition of the present invention can be used for aiding healing of intestinal wounds or ulcers in a patient suffering from same. Likewise, the composition can be used for preventing the onset of intestinal wounds or ulcers in a patient at risk of same. For these treatments, the composition can be administered alone.

Additionally, the composition of the present invention can be used to inhibit the gastrointestinal side effects suffered by a patient receiving a nonsteroidal anti-inflammatory drug. To this end, the composition of the present invention can be administered either contemporaneously or on the same days as the nonsteroidal anti-inflammatory drug.

Moreover, the composition of the present invention can be utilized in an improved method for treating patients suffering from arthritis. The method includes the step of administering the composition of the present invention in conjunction with the nonsteroidal anti-inflammatory drug, e.g., indomethacin. Again, the composition can be administered either contemporaneously or on the same days as the nonsteroidal anti-inflammatory drug.

By way of example, and not limitation, examples of suitable compositions that may be used pursuant to the present invention are as follows:

Composition No. 1

A suitable composition that may be utilized pursuant to the present invention is sold under the trademark Peptamen® and can be obtained from Clintec Nutrition Company. Peptamen® is a complete, liquid, ready-to-use, isotonic, peptide-based elemental diet. The Peptamen® elemental diet has a low osmolarity (270 mOsm/kg water) allowing feeding to be initiated at full strength.

Peptamen® includes the following ingredients: water; maltodextrin; hydrolyzed whey protein; mediumchain triglycerides (MCT source: fractionated coconut oil); corn starch; sunflower oil; soy lecithin; potassium citrate; sodium phosphate; magnesium chloride; guar gum; calcium phosphate; choline chloride; sodium ascorbate (vit. C); calcium citrate; magnesium oxide; taurine; L-carnitine; citric acid; zinc sulfate; ferrous sulfate; niacinamide (A B-vit); DL-alpha tocopheryl acetate (vit. E); rentinyl palmitate (vit. A); calcium pantothenate (A B- vit); manganese sulfate; pyridoxine hydrochloride (vit. $B_6$), cholecalciferol (vit. $D_3$); copper sulfate; riboflavin (vit. $B_2$); thiamine mononitrate (vit. $B_1$); folic acid; biotin; potassium iodide; sodium molybdate; phylloquinone (vit. $K_1$); sodium selanate; chromium chloride; and cyanocobalamin (vit. $B_{12}$).

Peptamen® has the following nutrient composition (based on 8.45 Fl oz (250 ml)):

| Nutrient Composition | Amount | % U.S. RDA* |
|---|---|---|
| Protein | 10 g | ** |
| Carbohydrate | 31.8 g | 22 |
| Fat*** | 9.8 g | ** |
| Water | 220 ml | ** |
| Vitamin A | 1000 I.U. | 20 |
| Vitamin D | 70 I.U. | 18 |
| Vitamin E | 7 I.U. | 23 |
| Vitamin K | 20 mcg | ** |
| Vitamin C | 35 mg | 58 |
| Thiamine ($B_1$) | .5 mg | 33 |
| Riboflavin ($B_2$) | .6 mg | 35 |
| Niacin | 7 mg | 35 |
| Vitamin $B_6$ | 1 mg | 50 |
| Folic Acid | 135 mcg | 34 |
| Pantoth Acid | 3.5 mg | 35 |
| Vitamin $B_{12}$ | 2 mcg | 33 |
| Biotin | 100 mcg | 33 |
| Choline | 112 mg | ** |
| Taurine | 20 mg | ** |
| L-Carnitine | 20 mg | ** |
| Calcium | 200 mg | 20 |
| Phosphorus | 175 mg | 18 |
| Magnesium | 100 mg | 25 |
| Zinc | 3.5 mg | 23 |
| Iron | 3 mg | 17 |
| Copper | .35 mg | 18 |
| Manganese | .68 mg | ** |
| Iodine | 25 mcg | 17 |
| Sodium | 125 mg | ** |
| Potassium | 313 mg | ** |
| Chloride | 250 mg | ** |
| Chromium | 10 mcg | ** |
| Molybdenum | 30 mcg | ** |
| Selenium | 10 mcg | ** |

*% U.S. RDA Recommended daily allowance for adults & children 4 or more years of age
**U.S. RDA not established
***MCT Provides 6.75 grams/250 ml

Composition No. 2

Another suitable composition that may be utilized in the present invention is sold under the trademark Nutren® 1.0. Nutren® 1.0 can also be obtained from Clintec Nutrition Company. Nutren® 1.0 is a balanced nutritional formula that is lactose and gluten-free.

Nutren® 1.0 includes the following ingredients: water; maltodextrin; calcium-potassium caseinate; canola oil; medium-chain triglycerides (MCT source: fractionated coconut oil); corn oil; sodium citrate; soy lecithin; potassium phosphate; citric acid; calcium citrate; potassium chloride; magnesium chloride; choline chloride; sodium ascorbate; sodium phosphate; carrageenan; magnesium oxide; L-carnitine; taurine; zinc sulfate; ferrous sulfate; DL-alpha tocopheryl acetate; niacinamide; retinyl palmitate; calcium pantothenate; manganese sulfate; pyridoxine hydrochloride; copper sulfate; riboflavin; thiamine; folic acid; biotin; cholecalciferol; potassium iodide; sodium molybdate; sodium selenate; phylloquinone; chromium chloride; and cyanocobalamin.

Nutren® 1.0 has the following nutrient composition (based on 8.45 Fl oz (250 ml)):

| Nutrient Composition | Amount | % U.S. RDA* |
|---|---|---|
| Protein | 10 g | ** |
| Carbohydrate | 31.8 g | 22 |
| Fat*** | 9.5 g | ** |
| Water | 213 ml | ** |
| Vitamin A | 1000 I.U. | 20 |
| Vitamin D | 70 I.U. | 17 |
| Vitamin E | 7 I.U. | 23 |
| ●Vitamin K | 12.5 mcg | ** |
| Vitamin C | 35 mg | 58 |
| Thiamine ($B_1$) | .5 mg | 33 |
| Riboflavin ($B_2$) | .6 mg | 35 |
| Niacin | 7 mg | 35 |
| Vitamin $B_6$ | 1 mg | 50 |
| Folic Acid | 135 mcg | 33 |
| Pantoth Acid | 3.5 mg | 35 |
| Vitamin $B_{12}$ | 2 mcg | 33 |
| Biotin | 100 mcg | 33 |
| Choline | 113 mg | ** |
| Taurine | 20 mg | ** |
| L-Carnitine | 20 mg | ** |
| ●Calcium | 167 mg | 17 |
| ●Phosphorus | 167 mg | 17 |
| ●Magnesium | 67 mg | 17 |
| Zinc | 3.5 mg | 23 |
| Iron | 3 mg | 17 |
| Copper | .35 mg | 17 |
| Manganese | .68 mg | ** |
| Iodine | 25 mcg | 17 |
| ●Sodium | 219 mg | ** |
| ●Potassium | 312 mg | ** |
| ●Chloride | 300 mg | ** |
| Chromium | 10 mcg | ** |
| Molybdenum | 30 mcg | ** |
| Selenium | 10 mcg | ** |

●Indicates modified levels
*% U.S. RDA recommended daily allowance for adults & children 4 or more years of age
**U.S. RDA not established
***MCT Provides 6.75 grams/250 ml By way of example, and not limitation, experimental results illustrating the use of the present invention to treat intestinal ulcers will now be set forth.

EXPERIMENT NO. 1

This experiment was conducted to evaluate whether two compositions would aid in the healing of indomethacin-induced ulceration in animals. The two compositions were Metronizadole, an antibiotic, and Petamen®.

A single injection of indomethacin (12.5 g/mg s.c.) was given to male Wistar rats, weighing approximately 300 grams. The control animals (N=10) received no treatment. Ten animals received metronidazole dosages of 32+/−4 mg/kg/day. Lastly, twelve animals received Peptamen® dosages of 57+/−1 ml/day. All except the animals treated with Peptamen® received rat chow ad libitum.

After fifteen (15) days, the animals were sacrificed, the intestine excised and the ulcer area measured by planimetry. A second control group was sacrificed after 60 days and tested similar to the other animals. Ulcer area was measured in $mm^2$. Table 1 below sets forth the test results.

TABLE 1

| Control (15 d.) | Metron. | Peptamen ® | Control (60 d.) |
|---|---|---|---|
| 166 +/− 42 | 191 +/− 59 | 17 +/− 7 | 477 +/− 185 |

As Table 1 illustrates, metronidazole did not effect the ulcer healing; whereas Petamen® significantly ($p<0.001$) reduced ulcer area. No spontaneous healing occurred since the ulcer area of the second control group at 60 days was similar to the control group at 15 days. While one animal that was unable to take adequate Peptamen® (31 ml/day, $p<0.005$) had extensive ulceration, three Peptamen® treated animals had a normal intestine, which was not detected with any other group. Accordingly, the composition of the present invention (Peptamen®) aids in the healing of intestinal ulcers.

EXPERIMENT NO. 2

This experiment was conducted to determine the effect of three compositions (Peptamen®, Nutren® and rat chow) on rats suffering intestinal ulceration. Each diet group consisted of five rats that were tested over a fifteen day exposure time.

All of the tested rats were initially administered a 12.5 mg/kg dosage of indomethacin to induce small intestinal ulcers. Then, over the fifteen days, each of the three group was feed the respective diet to compare the course of the ulcerations. The following parameters were recorded for each rat group over the fifteen day testing period: weight change (grams); daily caloric intake (cal); and ulcer area ($mm^2$).

Table 2 below sets forth the weights of the individual rats in each group, namely Peptamen®, Nutren® and rat chow, respectively, as well as the average of each group. Table 3 sets forth a comparison of the weights of the respective rats between groups and at the beginning and the end of the trial testing period. As these results demonstrate, no significant difference exists between the groups with regard to weight. However, rats in all groups weighed less at the end of the trial period than they did at the beginning.

TABLE 2

| Day | 0 | 4 | 6 | 8 | 11 | 13 | 15 | 18 |
|---|---|---|---|---|---|---|---|---|
| Peptamen (group avg) | 306 | 263 | 258 | 265.4 | 305.25 | 309.25 | 313 | 332.25 |
| Nutren (group avg) | 309.2 | 266 | 250 | 242.8 | 268.8 | 277.4 | 285.2 | 309.2 |
| rat chow (group avg) | 306 | 264.2 | 253.6 | 258.8 | 298.5 | 304 | 310.5 | 322.75 |
| Peptamen (individual weights) | | | | | | | | |
| A1 | 306 | 259 | 274 | 296 | 330 | 330 | 337 | 359 |
| A2 | 310 | 272 | 270 | 287 | 309 | 311 | 312 | 328 |
| A3 | 305 | 266 | 274 | 286 | 310 | 312 | 318 | 338 |
| A4 | 307 | 258 | 228 | 212 | | | | |
| A5 | 302 | 260 | 244 | 246 | 272 | 284 | 285 | 304 |
| Nutren (individual weights) | | | | | | | | |
| B1 | 300 | 249 | 250 | 241 | 275 | 283 | 297 | 320 |
| B2 | 314 | 257 | 237 | 230 | 247 | 265 | 264 | 286 |
| B3 | 305 | 267 | 239 | 225 | 233 | 244 | 248 | 278 |
| B4 | 317 | 275 | 250 | 240 | 281 | 288 | 300 | 322 |
| B5 | 310 | 2B2 | 274 | 278 | 308 | 307 | 317 | 340 |
| rat chow (individual weights) | | | | | | | | |
| C1 | 308 | 268 | 240 | 224 | | | | |
| C2 | 297 | 255 | 250 | 248 | 271 | 296 | 302 | 317 |
| C3 | 302 | 254 | 247 | 255 | 291 | 292 | 300 | 315 |
| C4 | 316 | 290 | 277 | 292 | 326 | 326 | 333 | 346 |
| C5 | 308 | 254 | 254 | 275 | 307 | 302 | 307 | 314 |

TABLE 3

| | Avg starting wt.(g) | Std dev | Avg wt. at the end | Std dev |
|---|---|---|---|---|
| Peptamen | 321.40 | 13.70 | 303.05 | 25.78 |
| Nutren | 324.42 | 14.74 | 295.53 | 23.74 |
| rat chow | 323.91 | 14.71 | 300.91 | 31.32 |

| | P values (for avg starting wts.) | P values (for avg ending wts) |
|---|---|---|
| Peptamen-Nutren | 0.51 | 0.33 |
| Peptamen-Chow | 0.56 | 0.80 |

| | P values (for difference between starting and ending wts.) |
|---|---|
| Peptamen | 8.77E-03 |
| Nutren | 9.26E-05 |
| rat chow | 4.01E-03 |

Figure 2:
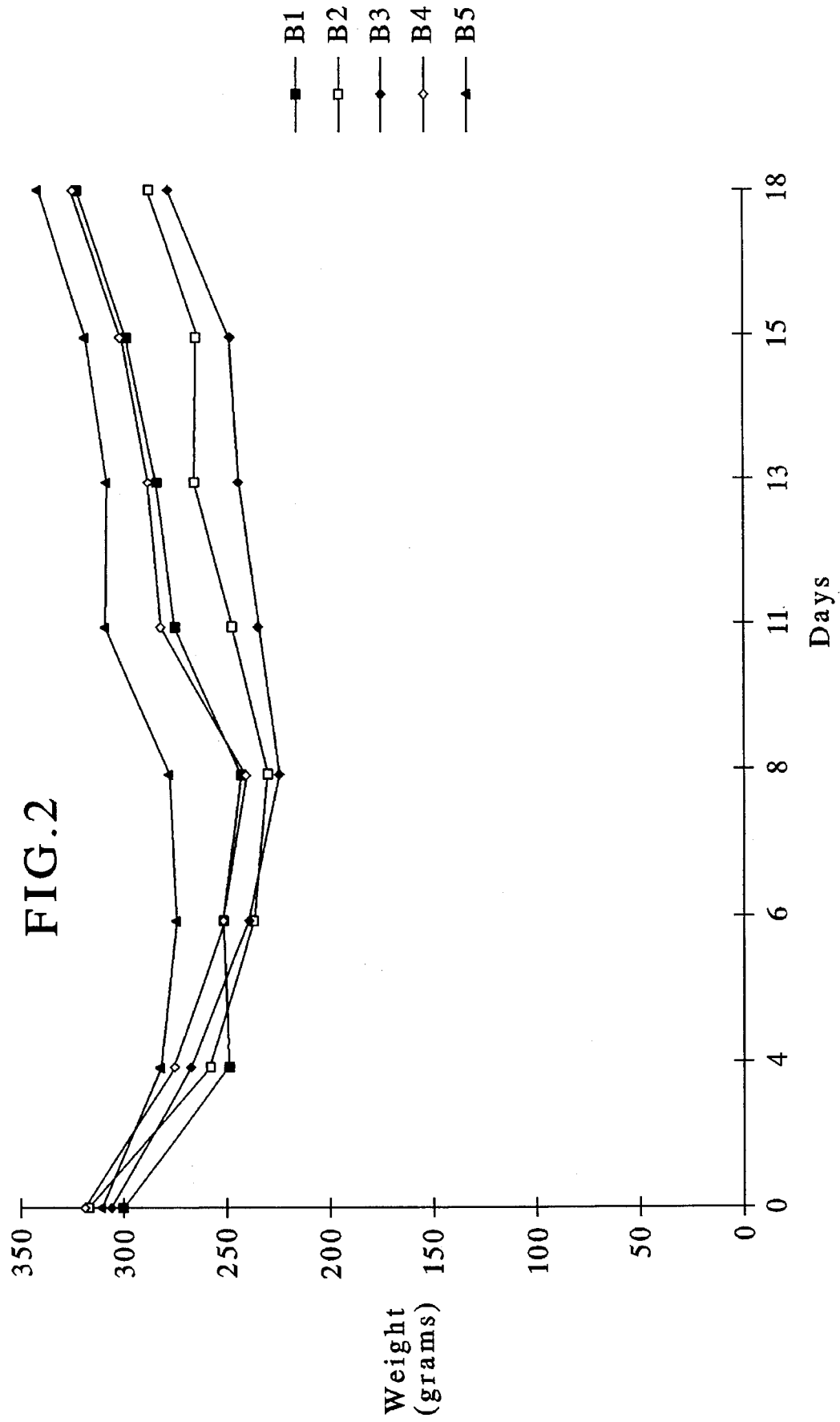
Figure 3:
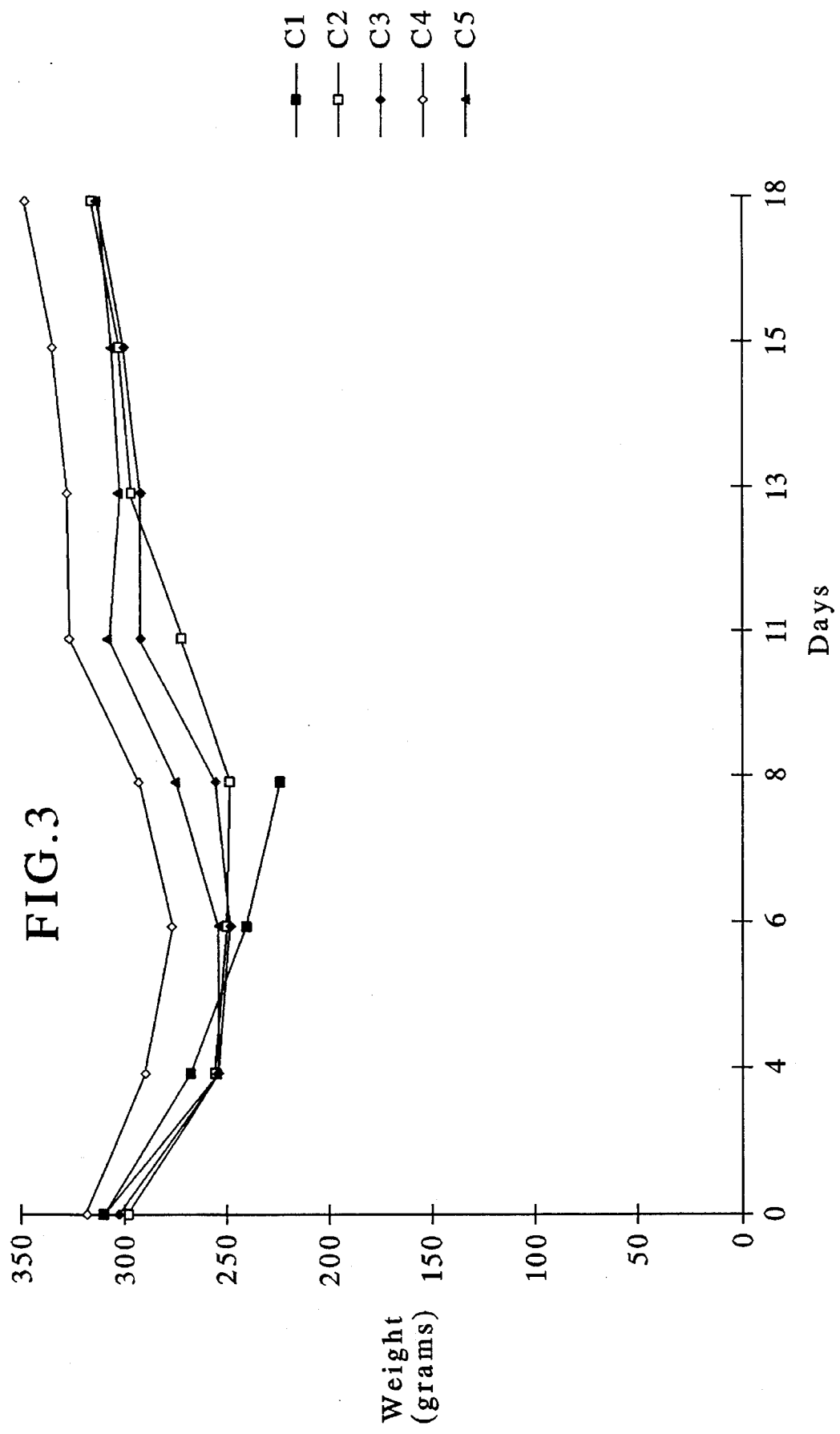
Figure 4:
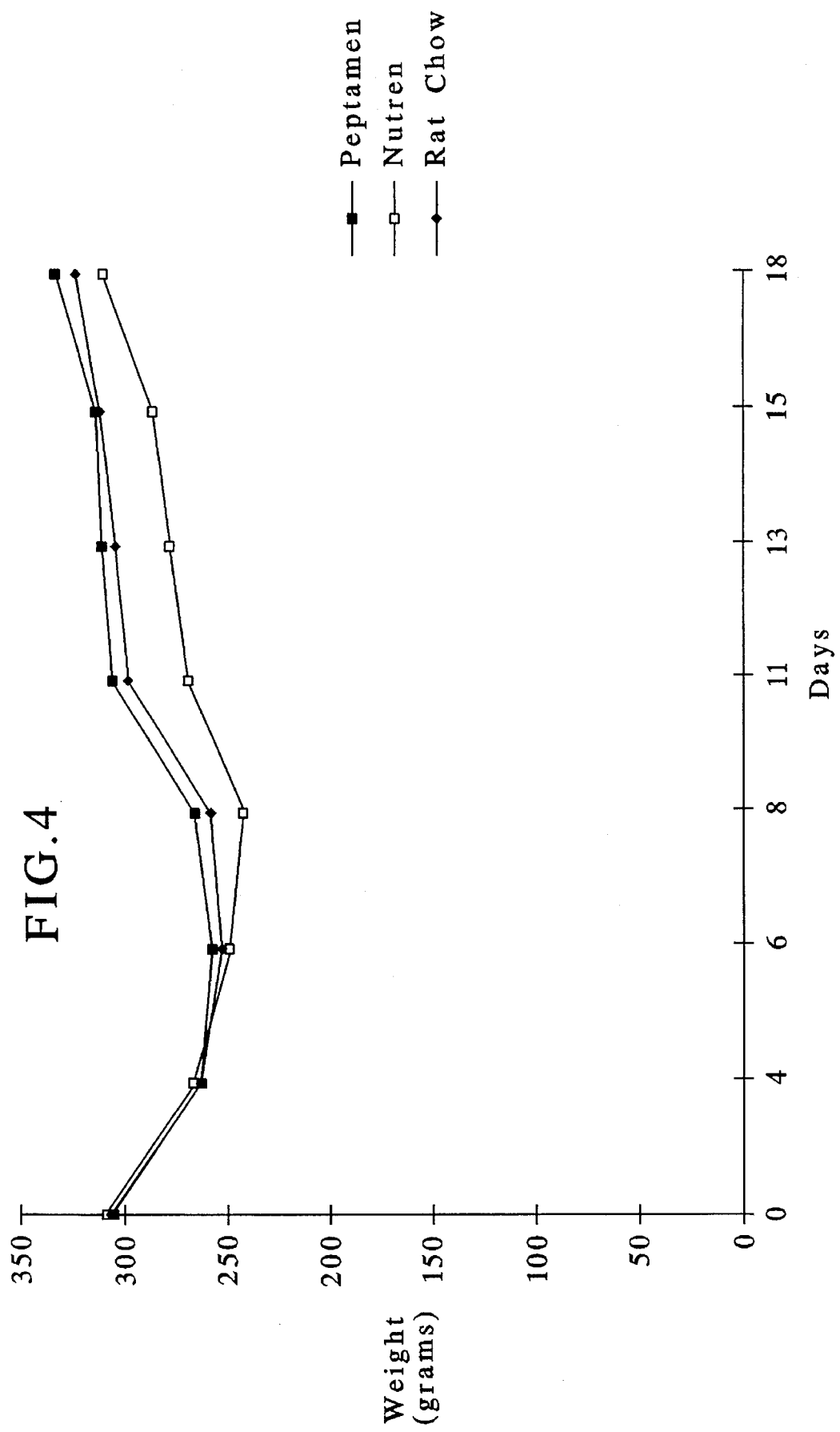
FIG. 4 illustrates the average weight in grams (gms) versus days of the three tested rat groups pursuant to Experiment No. 2.

FIGS. 1-3 graphically set forth the individual weights in weight (grams) versus days of the rats on the Peptamen®, Nutren® and standard rat chow respectively FIG. 4 is a graph of the average weight in weight (grams) versus days of the three groups. With respect to FIG. 4, the rats were injected with indomethacin on day 1 and the controlled diets began on day 4.

Tables 4A and 4B set forth the daily caloric intake (Kcal) for the rats administered the Peptamen®, Nutren® and rat chow diets. Day 1 represents 72 hours after the rats were injected with 12.5 mg/kg of indomethacin. On day 1, all rats were given 100 calories of the respective diets. On days 2 and 3, Bx and Cx were offered only as much as Ax ate on the previous day. On day 4, paired feeding was ok, A1 was offered 120 calories as it consistently ate all it was given; C4 and C5 were given as much as designed only on days 4–7 (to compensate for paired underfeeding on days 2 and 3). Otherwise, the rats were all offered 100 calories of the respective diets each day. Table 5 sets forth the average total caloric intake (over 15 days) of the three groups of rats.

TABLE 4A

| Day | 1 | 2 | 3 | 4 | 5 | 6 | 7 | 8 |
|---|---|---|---|---|---|---|---|---|
| Peptamen (group avg) | 55.8 | 53.8 | 61.2 | 78.8 | 91.75 | 94.75 | 92.75 | 97.25 |
| Nutren (group avg) | 48 | 35.2 | 28.2 | 61 | 76.4 | 82.6 | 84.4 | 91 |
| rat chow (group avg) | 59.2 | 45 | 36 | 103.6 | 113.8 | 117 | 116.5 | 101.75 |
| Peptamen (individual weights) | | | | | | | | |
| A1 | 73 | 96 | 96 | 121 | 112 | 115 | 110 | 115 |
| A2 | 62 | 58 | 72 | 89 | 89 | 92 | 88 | 91 |
| A3 | 75 | 76 | 81 | 98 | 87 | 90 | 92 | 91 |
| A4 | 12 | 7 | 15 | 12 | Sacrificed (gastric and duodenal dilation, mid-jejunal ulcer) | | | |
| A5 | 57 | 32 | 42 | 74 | 79 | 82 | 81 | 92 |

TABLE 4A-continued

| Day | 1 | 2 | 3 | 4 | 5 | 6 | 7 | 8 |
|---|---|---|---|---|---|---|---|---|
| Nutren (Individual intake) | | | | | | | | |
| B1 | 57 | 60 | 52 | 50 | 83 | 94 | 93 | 93 |
| B2 | 27 | 22 | 20 | 42 | 80 | 80 | 84 | 92 |
| B3 | 23 | 26 | 30 | 29 | 50 | 57 | 56 | 73 |
| B4 | 38 | 12 | 8 | 86 | 77 | 88 | 95 | 100 |
| B5 | 95 | 56 | 31 | 98 | 92 | 94 | 94 | 97 |
| rat chow (Individual intake) | | | | | | | | |
| C1 | 10 | 22 | 18 | 26 | 0 | Sacrificed (gastric and duodenal dilation, distal duodenal mass) | | |
| C2 | 66 | 66 | 62 | 88 | 102 | 102 | 102 | 101 |
| C3 | 44 | 62 | 57 | 84 | 102 | 102 | 102 | 102 |
| C4 | 101 | 13 | 8 | 162 | 175 | 132 | 132 | 102 |
| C5 | 76 | 62 | 35 | 158 | 190 | 132 | 30 | 102 |

TABLE 4B

| Day | 9 | 10 | 11 | 12 | 13 | 14 | 15 |
|---|---|---|---|---|---|---|---|
| Peptamen (group avg) | 90.75 | 96.5 | 92.75 | 90.5 | 96 | 96.25 | 96.5 |
| Nutren (group avg) | 90.8 | 91.4 | 89.8 | 93 | 92.6 | 96 | 94.2 |
| rat chow (group avg) | 102 | 102 | 102 | 102 | 102 | 102 | 102 |
| Peptamen (individual weights) | | | | | | | |
| A1 | 109 | 116 | 111 | 107 | 115 | 111 | 108 |
| A2 | 78 | 91 | 91 | 88 | 92 | 93 | 91 |
| A3 | 89 | 92 | 87 | 85 | 89 | 95 | 92 |
| A4 | Sacrificed (gastric and duodenal dilation, mid-jejunal ulcer) | | | | | | |
| A5 | 87 | 87 | 82 | 82 | 88 | 86 | 95 |
| Nutren (Individual intake) | | | | | | | |
| B1 | 93 | 92 | 92 | 93 | 90 | 96 | 95 |
| B2 | 97 | 89 | 87 | 95 | 97 | 100 | 92 |
| B3 | 73 | 78 | 81 | 87 | 87 | 91 | 94 |
| B4 | 96 | 100 | 91 | 92 | 91 | 94 | 94 |
| B5 | as | 98 | 98 | 98 | 98 | 99 | 96 |
| rat chow (Individual Intake) | | | | | | | |
| C1 | Sacrificed (gastric and duodenal dilation, distal duodenal mass) | | | | | | |
| C2 | 102 | 102 | 102 | 102 | 102 | 102 | 102 |
| C3 | 102 | 102 | 102 | 102 | 102 | 102 | 102 |
| C4 | 102 | 102 | 102 | 102 | 102 | 102 | 10 |
| C5 | 102 | 102 | 102 | 102 | 102 | 102 | 102 |

TABLE 5

| | Total Cals | Std dev |
|---|---|---|
| Peptamen | 982.95 | 224.68 |
| Nutren | 953.26 | 172.95 |
| rat chow | 966.74 | 173.85 |
| P values | | |
| Peptamen-Nutren | 0.64 | |
| Peptamen-Chow | 0.79 | |
| Nutren-Chow | 0.80 | |

Figure 5:
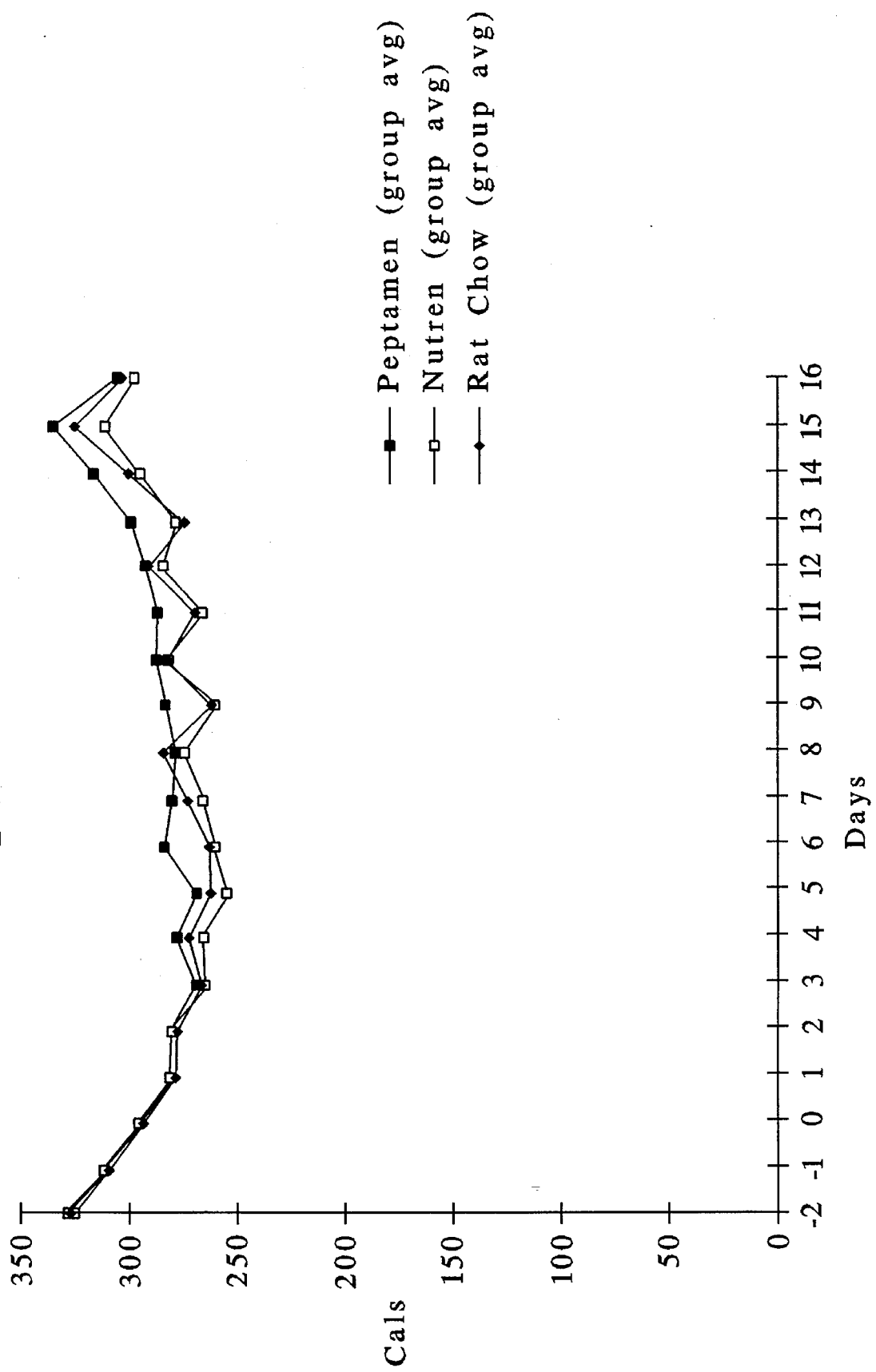
FIG. 5 illustrates the average caloric intake in calories (cals) versus days of the three tested rat groups pursuant to Experiment No. 2.
Figure 6:
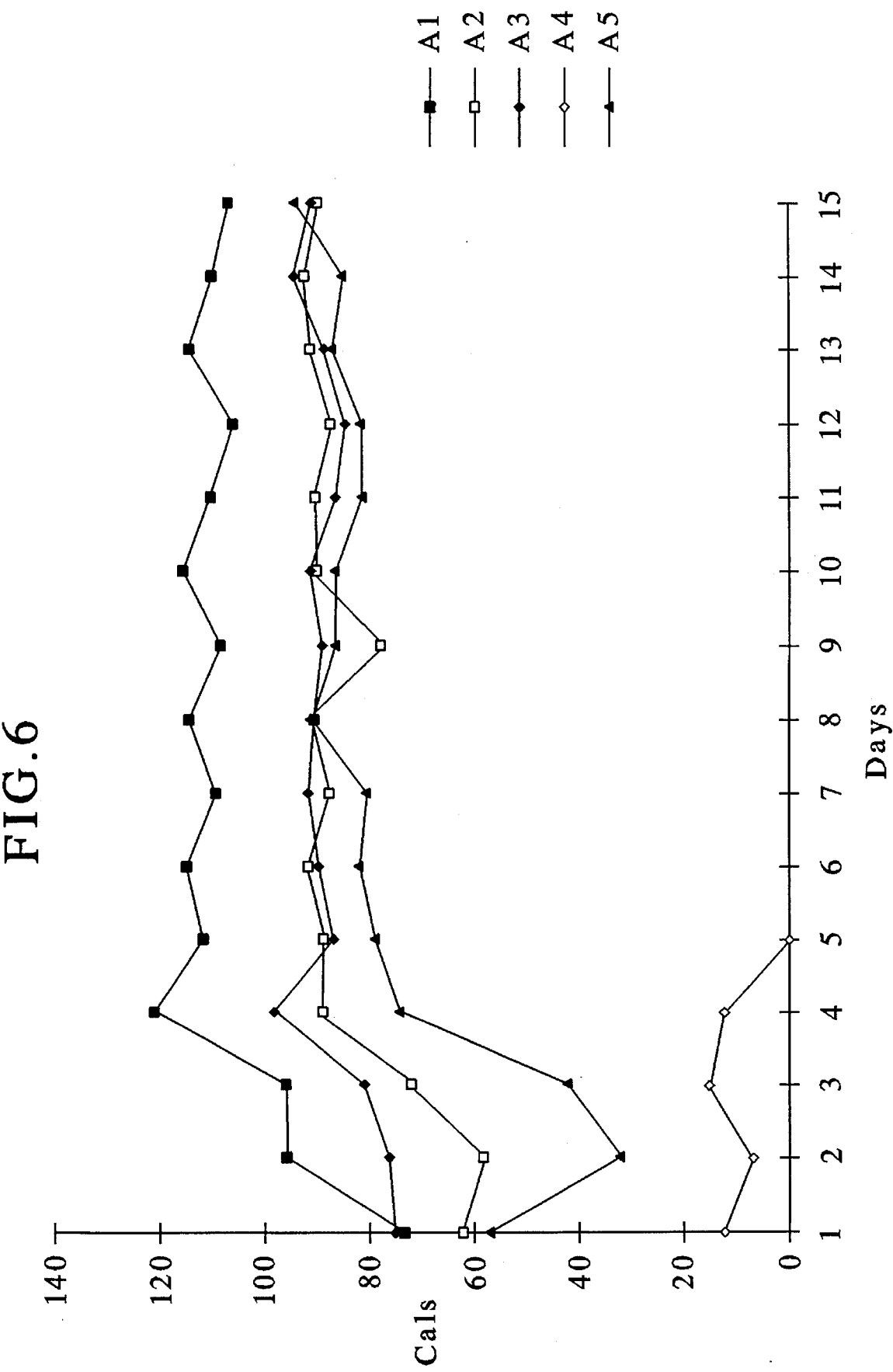
FIG. 6–8 illustrate the caloric intake in calories (cals) versus days of the rats administered Peptamen®, Nutren® and standard rat chow, respectively, pursuant to Experiment No. 2.
Figure 7:
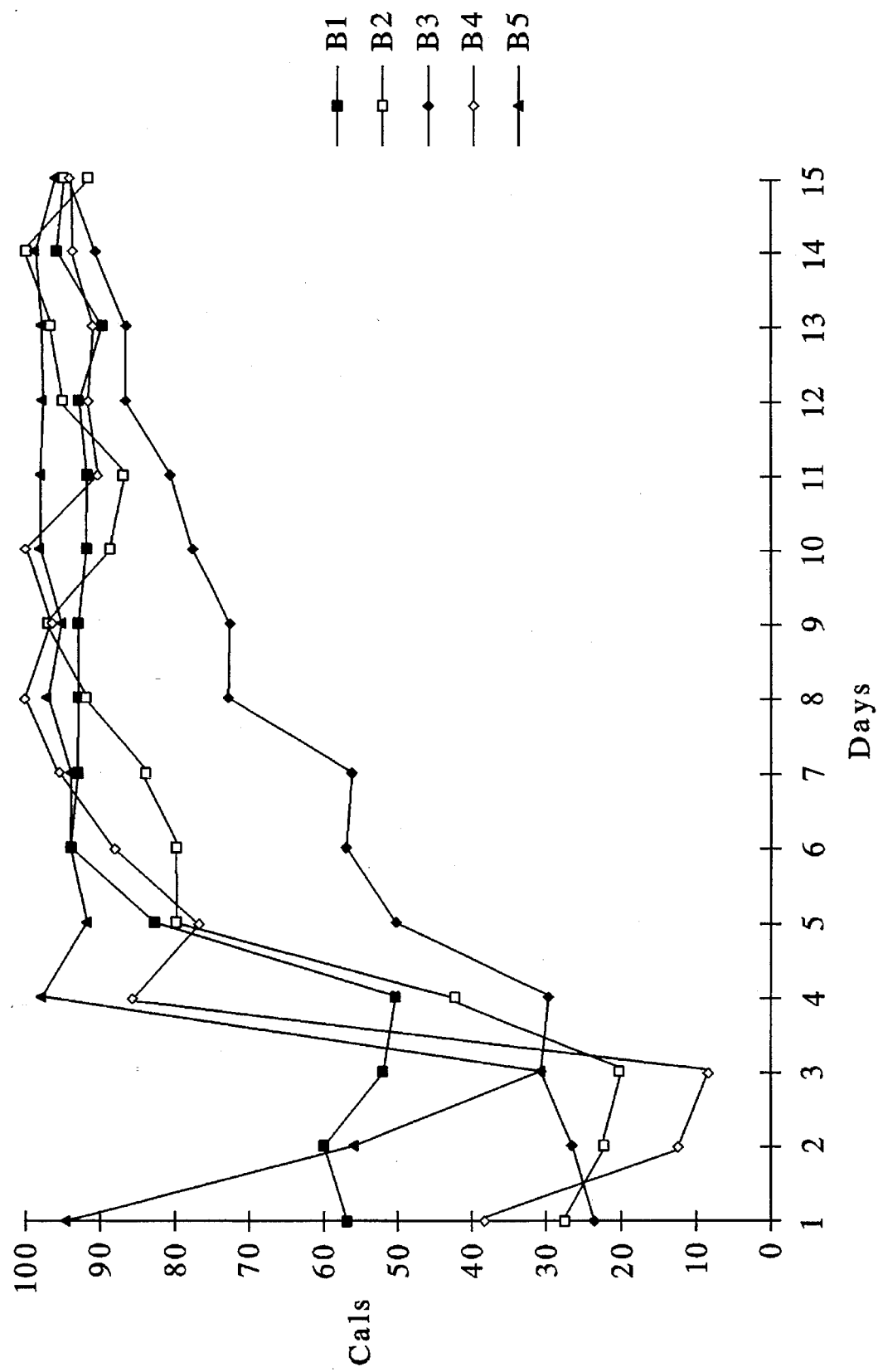
Figure 8:
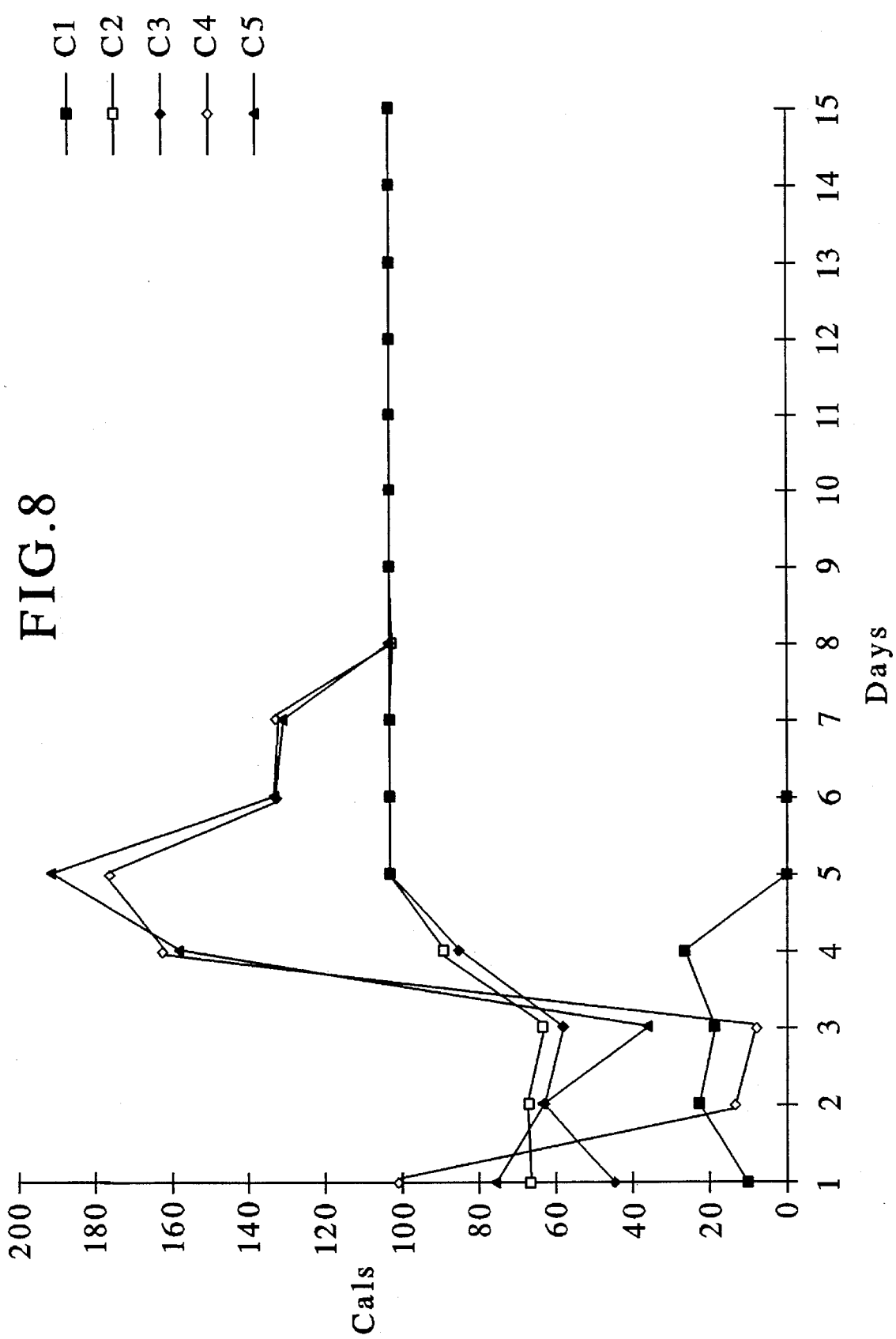
Figure 9:
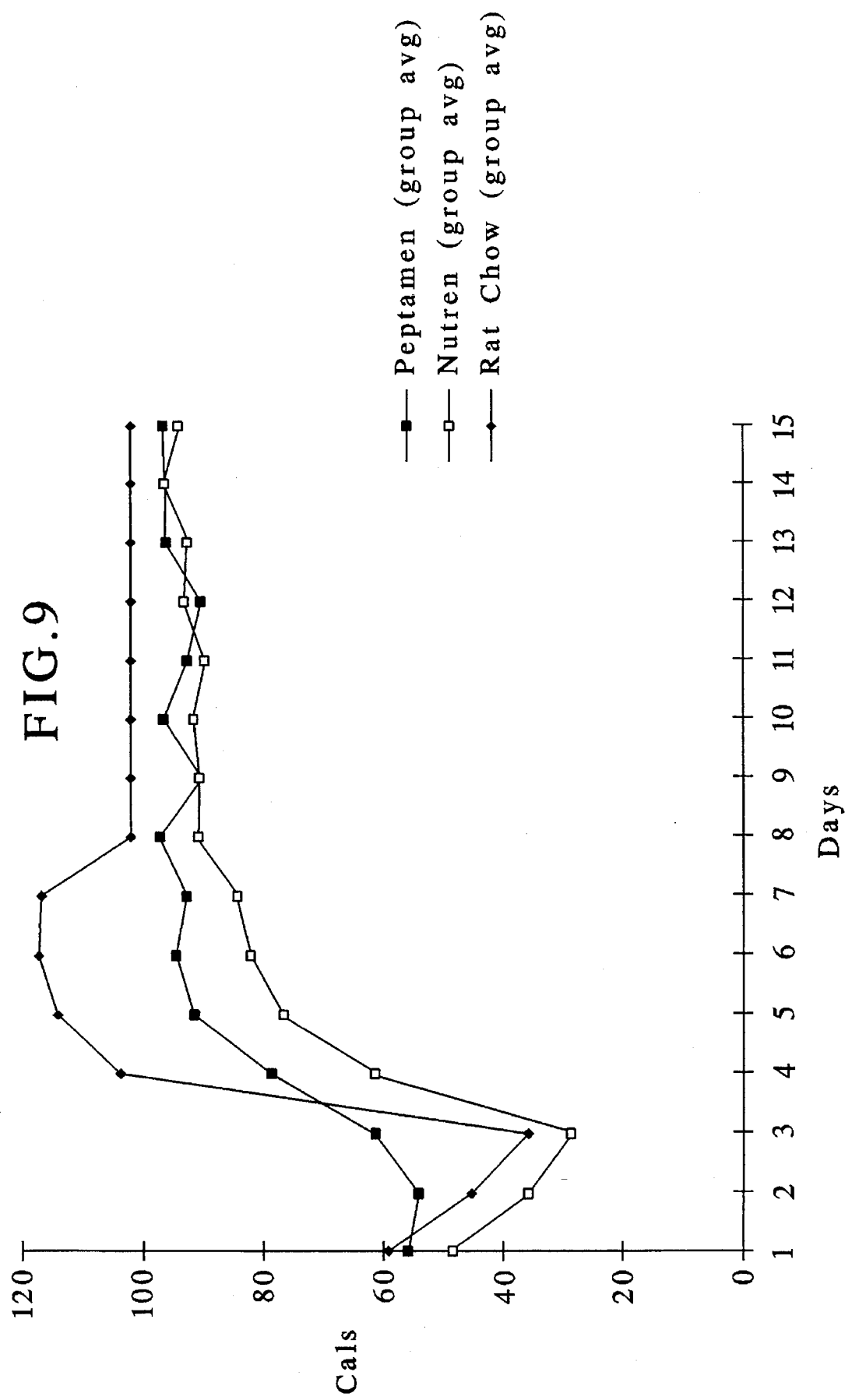
FIG. 9 illustrates the average caloric intake in calories (cals) versus days of the three tested rat groups pursuant to Experiment No. 2.
Figure 10:
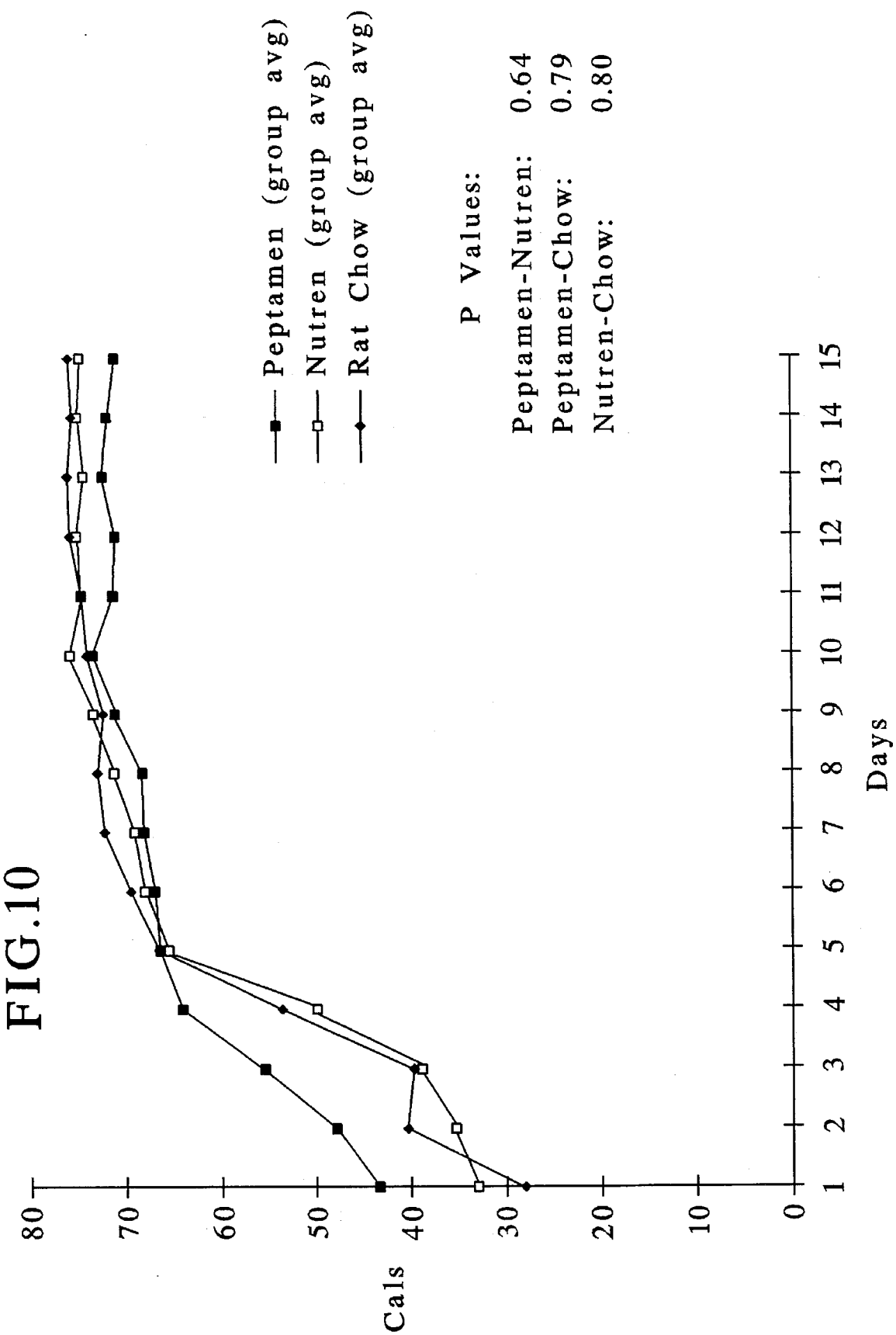
FIG. 10 illustrates the average caloric intake in calories of metabolizable energy versus days of the three tested rat groups pursuant to Experiment No. 2.

FIG. 5 is a graph of the average caloric intake in calories versus days of the three groups. With respect to this figure, one should note that rats were first weighed on the day of injection (day −2). Day 1 is the first day of the controlled diets. FIGS. 6–8 graphically detail the caloric intake in calories versus days of the rats administered Peptamen®, Nutren® and standard rat chow, respectively. FIG. 9 is a graph detailing the average caloric intake in calories versus days of the three groups. FIG. 10 is a graph detailing the average caloric intake in calories of metabolizable energy versus days of the three groups.

Figure 11:
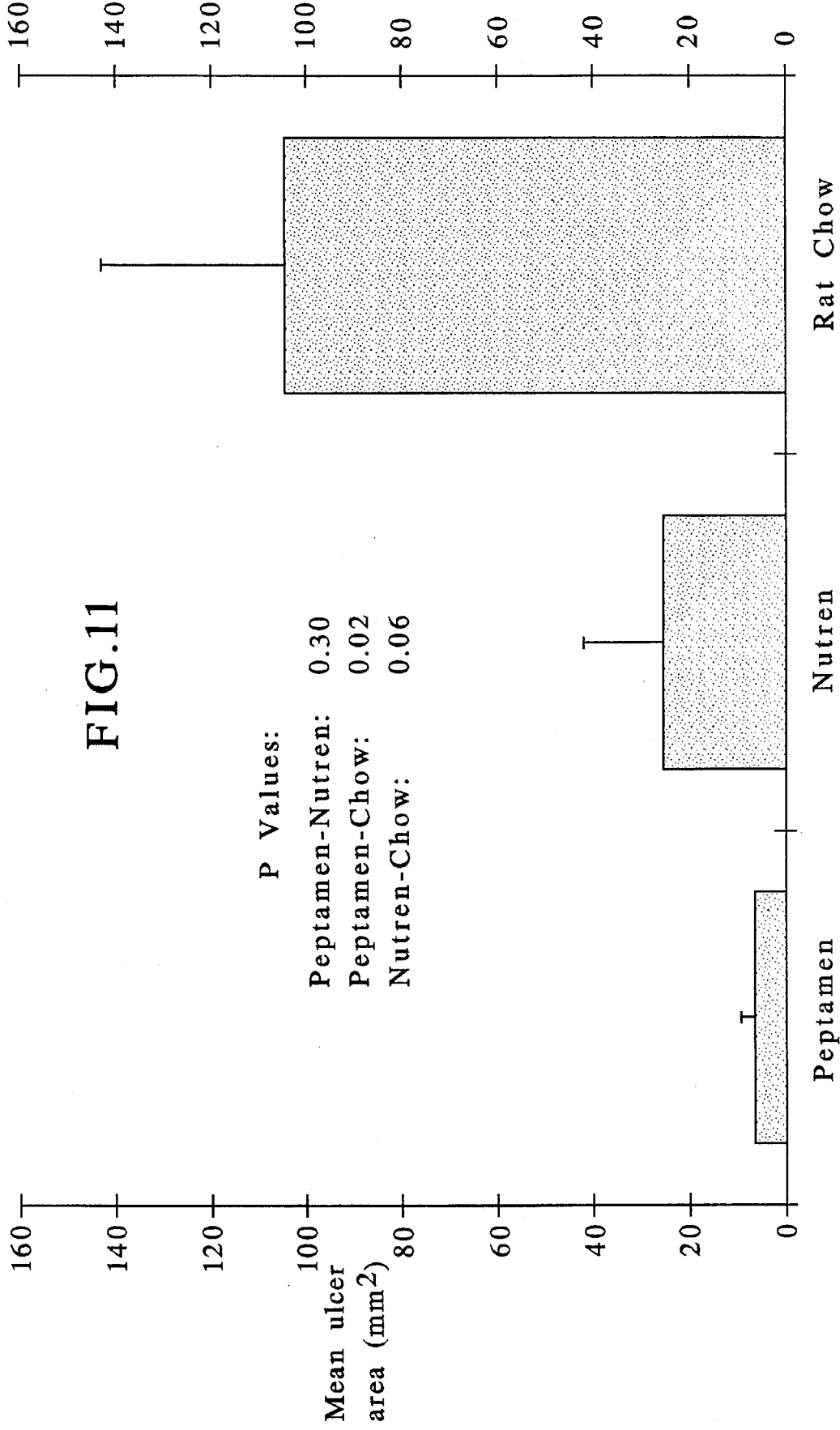
FIG. 11 is a bar graph representing the mean ulcer area ($mm^2$) of the three tested rat groups pursuant to Experiment No. 2.
Figure 12:
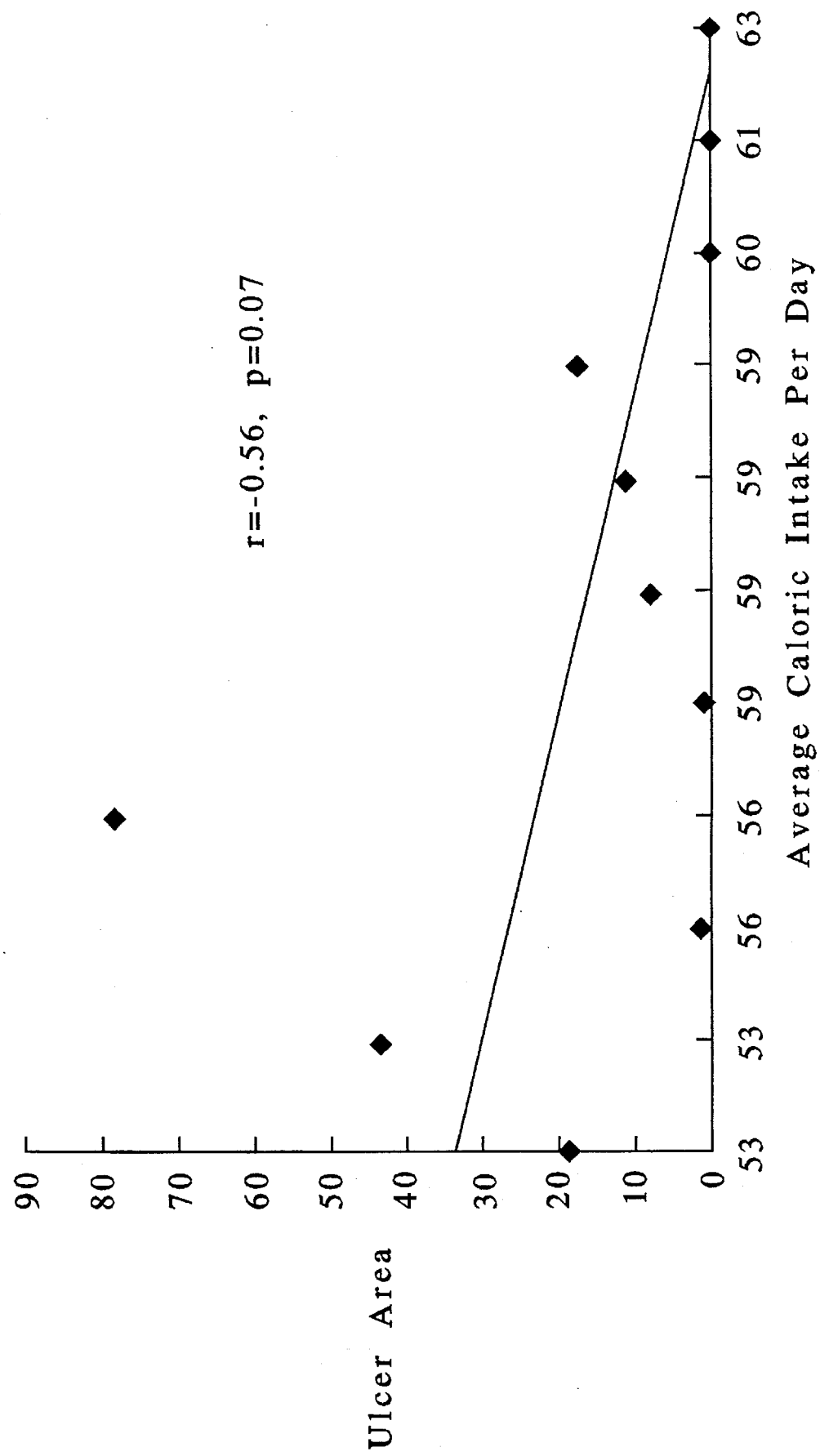
FIG. 12 illustrates the relationship between ulcer area and average caloric intake per day for the tested rat groups pursuant to Experiment No. 1.

Lastly, the ulcer area ($mm^2$) was measured for each rat by planimetry. FIG. 11 is a bar graph representing the mean ulcer area ($mm^2$) of the three groups. FIG. 12 graphically represents the relationship between ulcer area and average caloric intake per day of the rats.

It will be understood that various modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

I claim:

1. A method for aiding healing of intestinal wounds or ulcers in a patient receiving a non-steroidal anti-inflammatory drug comprising the step of administering to the patient a therapeutically effective amount of a composition comprising:

a protein source comprising approximately 14% to about 25% of the total calories;

a carbohydrate source comprising approximately 40% to about 60% of the total calories; and a fat source comprising approximately 33% to about 44% of the total calories, the fat source including a medium-chain triglyceride to long chain triglyceride ratio of approximately 1:4 to 4:1.

2. The method of claim 1 wherein the protein source includes hydrolyzed whey.

3. The method of claim 1 wherein the protein source includes casein.

4. The method of claim 1 wherein the carbohydrate source is selected from the group consisting of: maltodextrin and corn starch.

5. The method of claim 1 wherein the fat source includes approximately 25% to 75% medium chain triglycerides.

6. The method of claim 1 wherein the composition includes fractionated coconut oil as a source of medium chain triglycerides.

7. The method of claim 1 wherein the composition is administered enterally.

8. A method for inhibiting the gastrointestinal side effects suffered by a patient receiving a nonsteroidal anti-inflammatory drug comprising the step of administering to the patient a therapeutically effective amount of a composition comprising:

a protein source comprising approximately 14% to about 25% of the total calories;

a carbohydrate source comprising approximately 40% to about 60% of the total calories;

a fat source comprising approximately 33% to about 44% of the total calories, the fat source including a medium-chain triglyceride to long chain triglyceride ratio of approximately 1:4 to 4:1; and a source of vitamins and minerals including approximately 75% to about 150% of the recommended daily allowance per 1500 Kcal of the composition administered.

9. The method of claim 8 wherein the protein source includes hydrolyzed whey.

10. The method of claim 8 wherein the protein source includes casein.

11. The method of claim 8 wherein the carbohydrate source is selected from the group consisting of: maltodextrin and corn starch.

12. The method of claim 8 wherein the fat source includes approximately 25% to 75% medium chain triglycerides.

13. The method of claim 8 wherein the composition includes fractionated coconut oil as a source of medium chain triglycerides.

14. The method of claim 8 wherein the composition is administered enterally.

15. The method of claim 8 wherein the composition is administered contemporaneously with the nonsteroidal anti-inflammatory drug.

16. The method of claim 8 wherein the nonsteroidal anti-inflammatory drug is indomethacin.

17. The method of claim 8 wherein the composition is administered on the same day as the nonsteroidal anti-inflammatory drug.

18. A method for treating arthritis in a patient suffering from same comprising the steps of:

administering a therapeutically effective amount of a nonsteroidal anti-inflammatory drug; and administering a therapeutically effective amount of a composition comprising:

a protein source comprising approximately 14% to about 25% of the total calories;

a carbohydrate source comprising approximately 40% to about 60% of the total calories; and a fat source comprising approximately 33% to about 44% of the total calories, the fat source including a medium-chain triglyceride to long chain triglyceride ratio of approximately 1:4 to 4:1.

19. The method of claim 18 wherein the composition is administered enterally.

* * * * *